United States Patent [19]

Dorn et al.

[11] Patent Number: 4,678,790
[45] Date of Patent: Jul. 7, 1987

[54] CERTAIN α-BENZYL-3-PYRIDYLMETHANOLS, N-OXIDES THEREOF AND THEIR FUNGICIDAL USE

[75] Inventors: Franz Dorn, Dielsdorf; Albert Pfiffner, Bülach; Beat Zehnder, Kaiseraugst, all of Switzerland

[73] Assignee: Hoffman-La Roche Inc., Nutley, N.J.

[21] Appl. No.: 655,812

[22] Filed: Oct. 1, 1984

[30] Foreign Application Priority Data

Oct. 7, 1983 [CH] Switzerland ............... 5458/83
Jul. 26, 1984 [CH] Switzerland ............... 3620/84

[51] Int. Cl.$^4$ ............... C07D 213/30; A01N 43/40
[52] U.S. Cl. ............... 514/277; 514/357; 544/336; 546/333; 546/334; 546/343; 546/344
[58] Field of Search ............... 546/344, 343, 333, 334; 514/277, 357

[56] References Cited

U.S. PATENT DOCUMENTS 3,409,629  11/1968  Biel et al. ............... 546/343

OTHER PUBLICATIONS

Buschmann et al., Chem. Abstracts, vol. 98, (23), Abst. No. 198,037g, Jun. 6, 1983.
Van Heyningen et al., Chem. Abstracts, vol. 69, (23), Abst. No. 96485k, Dec. 2, 1968.
Van Heyninggen et al., Chem. Abstracts, vol. 72 (15), Abst. No. 78,897d, Apr. 13, 1970.

*Primary Examiner*—Alan L. Rotman
*Attorney, Agent, or Firm*—Jon S. Saxe; George M. Gould; Dennis P. Tramaloni

[57] ABSTRACT

Novel pyridine, pyrazine and pyrimidine derivatives of the formula

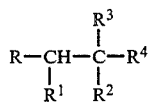

wherein R, $R^1$, $R^2$, $R^3$ and $R^4$ are as hereinafter set forth, and acid addition salts thereof, processes for their preparation, fungicidal compositions containing these compounds as the active ingredient as well as the use of such compounds or compositions for the control of fungi in agriculture and in horticulture are disclosed.

19 Claims, No Drawings

CERTAIN α-BENZYL-3-PYRIDYLMETHANOLS, N-OXIDES THEREOF AND THEIR FUNGICIDAL USE

SUMMARY OF THE INVENTION

The invention relates to novel pyridine, pyrazine and pyrimidine derivatives of the formula

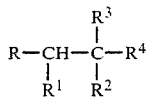

wherein R, $R^1$, $R^2$ and $R^3$ are as described hereafter and $R^4$ is 3-pyridyl, 3-pyridyl 1-oxide, 2-pyrazinyl, 2-pyrazinyl 1-oxide, 2-pyrazinyl 4-oxide, 2-pyrazinyl 1,4-dioxide, 5-pyrimidinyl, 5-pyrimidinyl 1-oxide or 5-pyrimidinyl 1,3-dioxide, and acid addition salts of these compounds.

The invention is also directed to fungicidal compositions containing, as the active ingredient, at least one of the compounds of formula I and methods of combatting fungi in agriculture and in horticulture.

DETAILED DESCRIPTION OF THE INVENTION

The present invention comprises heterocyclic compounds, especially pyridine, pyrazine and pyrimidine derivatives of the formula

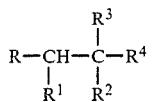

wherein R is mono-, di- or trisubstituted phenyl, the phenyl group being substituted with 1–3 halogen atoms and/or 1 or 2 $C_{1-3}$-alkyl groups and/or 1 or 2 $C_{1-3}$-alkoxy groups and/or 1 or 2 trifluoromethyl groups. $R^1$ is $C_{1-6}$-alkyl, $C_{3-6}$-alkenyl, $C_{3-6}$-alkynyl, $C_{1-6}$-alkylthio, $C_{3-6}$-alkenylthio or $C_{3-6}$-alkynylthio optionally substituted with a $C_{1-4}$-alkoxy group; or optionally mono-, d- or tri-substituted arylthio, the optionally present substituents being 1 to 3 halogen atoms and/or 1 or 2 $C_{1-3}$-alkyl groups and/or 1 or 2 $C_{1-3}$-alkoxy groups and/or a nitro group, $R^2$ is hydroxy, chlorine or bromine, $R^3$ is $C_{2-6}$-alkenyl; aryl or aryl- $C_{1-3}$-alkyl optionally mono-, di- or trisubstituted in the aryl nucleus, the optionally present substituents being 1–3 halogen atoms and/or 1 or 2 $C_{1-3}$-alkyl groups and/or 1 or 2 $C_{1-3}$-alkoxy groups and/or a nitro group; or a group C≡$CR^5$, $R^4$ is 3-pyridyl, 3-pyridyl 1-oxide, 2-pyrazinyl, 2-pyrazinyl 1-oxide, 2-pyrazinyl 4-oxide, 2-pyrazinyl 1,4-dioxide, 5-pyrimidinyl, 5-pyrimidinyl 1-oxide or 5-pyrimidinyl 1,3-dioxide and $R^5$ is hydrogen; $C_{1-10}$-alkyl optionally substituted with 1 or 2 $C_{1-3}$-alkoxy groups, a chlorine atom or a bromine atom; vinyl; $C_{1-6}$-alkoxy; bromine; iodine; or optionally mono-, di- or trisubstituted aryl, the optionally present substituents being 1–3 halogen atoms and/or 1 or 2 $C_{1-3}$-alkyl groups and/or 1 or 2 $C_{1-3}$-alkoxy groups, and acid addition salts of these compounds.

The compounds of formula I and their acid addition salts possess fungicidal properties and are suitable as fungicidal agents, especially for use in agriculture and in horticulture.

Fungicidal compositions containing compounds of formula I and acid addition salts thereof, as well as methods for their use in combatting plant fungi, are also encompassed within the scope of this invention.

The term "halogen" in formula I above embraces fluorine, chlorine, bromine and iodine. The alkyl, alkenyl and alkynyl groups can be straight-chain or branched-chain and this also applies to the alkyl, alkenyl or alkynyl part of the alkoxy, arylalkyl, alkylthio, alkenylthio and alkynylthio groups. The term "aryl" per se or as part of "arylthio" or "aryl-$C_{1-3}$alkyl" preferably denotes phenyl, although heterocyclic groups having aromatic character such as pyridyl, furyl and thienyl are also contemplated. In di- or trisubstituted phenyl, arylthio, aryl, arylalkyl or alkyl the substituents can be the same or different.

An interesting sub-group of compounds of formula I comprises those compounds of formula I in which R is mono-, di- or trihalophenyl; $R^1$ is unsubstituted $C_{1-6}$-alkyl, $C_{3-6}$-alkenyl, $C_{3-6}$-alkynyl or $C_{1-6}$-alkylthio; $R^2$ is hydroxy or chlorine; $R^3$ is $C_{2-6}$-alkenyl, optionally substituted aryl, as more precisely defined above, or a group C≡$CR^5$ in which $R^5$ is hydrogen, optionally substituted $C_{1-10}$-alkyl, as more precisely defined above, $C_{1-6}$-alkoxy, bromine, iodine or optionally substituted aryl, as more precisely defined above; and $R^4$ is 3-pyridyl, 2-pyrazinyl or 5-pyrimidinyl.

Independently of each other R is preferably mono-, di- or trihalophenyl, especially 2,4-dichlorophenyl, and $R^4$ is preferably 3-pyridyl, 2-pyrazinyl or 5-pyrimidinyl, especially 3-pyridyl or 2-pyrazinyl.

Especially preferred compounds of formula I are:
α-Ethynyl-α-(2,4-dichloro-α-methylbenzyl)-3-pyridylmethanol,
α-(2,4-dichloro-α-methylbenzyl)-α-(1-pentynyl)-3-pyridylmethanol,
α-(2,4-dichloro-α-methylbenzyl)-α-iodoethynyl-3-pyridylmethanol,
α-(2,4-dichloro-α-methylbenzyl)-α-vinyl-3-pyridylmethanol,
α-ethynyl-α-(2,4-dichloro-α-methylthio-benzyl)-3-pyridylmethanol,
α-ethoxyethynyl-α-(2,4-dichloro-α-methylbenzyl)-3-pyridylmethanol,
α-ethynyl-α-[2,4-dichloro-α-(2-propynyl)-benzyl]-3-pyridylmethanol,
α-(2,4-dichloro-α-methylbenzyl)-α-(1-propen-1-yl)-3-pyridylmethanol,
α-(2,4-dichloro-α-methylbenzyl)-α-isopropenyl-3-pyridylmethanol and
α-(2,4-dichloro-α-methylbenzyl)-α-[(Z)-1-pentenyl]-3-pyridylmethanol.

Further representative compounds of formula I are:
α-Ethynyl-α-(2,4-dichloro-α-methylbenzyl)-5-pyrimidylmethanol,
α-ethynyl-α-(2,4-dichloro-α-methylbenzyl)-2-pyrazinylmethanol,
α-(but-3-en-1-ynyl)-α-(2,4-dichloro-α-methylbenzyl)-3-pyridylmethanol,
α-(2,4-dichloro-α-methylbenzyl)-α-vinyl-5-pyrimidinylmethanol and
α-(2,4-dichloro-α-methylbenzyl)-α-vinyl-2-pyrazinylmethanol.

Since the compounds of formula I can have at least one asymmetric carbon atom, the compounds can exist in isomeric forms. In addition, geometric isomerism can also exist due to the presence of an aliphatic carbon-carbon double bond. Formula I is intended to include all of these possible isomeric forms.

As acid addition salts of the compounds of formula I which come into consideration as physiologically compatible salts. These salts are preferably salts of the compounds of formula I with inorganic and organic acids such as hydrochloric acid, nitric acid, phosphoric acid, mono- and bifunctional carboxylic acids and hydroxycarboxylic acids (e.g. acetic acid, maleic acid, succinic acid, fumaric acid, tartaric acid, citric acid, salicylic acid, sorbic acid and lactic acid) and sulfonic acids (e.g. 1,5-naphthalenedisulfonic acid). In the case of the N-oxides, i.e. the compounds of formula I in which $R^4$ is 3-pyridyl 1-oxide, 2-pyrazinyl 1-oxide, 4-oxide and 1,4-dioxide, and 5-pyrimidinyl 1-oxide and 1,3-dioxide, examples of acid addition salts include physiologically compatible salts with strong acids such as inorganic acids, e.g. hydrochloric acid, nitric acid and phosphoric acid, and sulfonic acids, e.g. 1,5-naphthalenedisulfonic acid.

The compounds of formula I are prepared by one of the procedures described hereinafter.

(A) For the preparation of the compounds of formula I in which $R^2$ is hydroxy, $R^4$ is 3-pyridyl, 2-pyrazinyl or 5-pyrimidinyl and $R^3$ is as previously defined with the exception of C≡CBr or C≡CI, a ketone of the formula

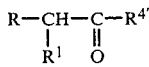
II wherein R and $R^1$ are as previously defined and $R^{4'}$ is 3-pyridyl, 2-pyrazinyl or 5-pyrimidinyl, is reacted with a compound of the formula $(R^{3'})_nX$                          III wherein $R^{3'}$ is defined for $R^3$ with the exception of C≡CBr or C≡CI, X is an alkali metal, e.g. lithium, sodium or potassium, an alkaline earth metal, e.g. calcium or magnesium, or MgHal, n is the valency of X and Hal is halogen, especially bromine or iodine.

This procedure is conveniently carried out by reacting the ketone of formula II with the compound of formula III in an inert diluent, preferably an aprotic solvent such as an aliphatic or cyclic ether, e.g. diethyl ether, tetrahydrofuran or dioxan. The reaction is conveniently carried out in a temperature range between −80° C. and the reflux temperature of the reaction mixture, preferably between −80° C. and 0° C. (where X=lithium) or between 0° C. and the reflux temperature (where X=MgHal). In many cases it has been found to be advantageous to use the compound of formula III in excess, namely up to 200 mol percent. In formula III X is preferably lithium or MgHal.

(B) For the preparation of the compounds of formula I in which $R^2$ is hydroxy, $R^3$ is the group C≡CBr or C≡CI and $R^4$ is 3-pyridyl, 2-pyrazinyl or 5-pyrimidinyl, an ethyne derivative of the formula

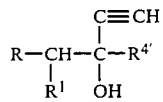
I′ wherein R, $R^1$ and $R^{4'}$ are as previously defined, is treated with a brominating or iodinating agent.

This procedure is conveniently carried out by treating the ethyne derivative of formula I′ with the brominating or iodinating agent, preferably elementary bromine or iodine, in an inert diluent in the presence of a base. Depending on the type of base the reaction is carried out at temperatures between −80° C. and the reflux temperature of the reaction mixture. The diluent is preferably an organic solvent such as an aliphatic or aromatic hydrocarbon, e.g. n-hexane, benzene, toluene or a xylene; a halogenated aromatic hydrocarbon, e.g. chlorobenzene; a tertiary amine, e.g. triethylamine or pyridine; an aliphatic or araliphatic alcohol, e.g. methanol, ethanol, n-propanol, isopropanol or benzyl alcohol; or an aliphatic or cyclic ether, e.g. diethyl ether, butyl methyl ether, dioxan or tetrahydrofuran. Preferred bases are alkali metal hydroxides, e.g. sodium hydroxide, alkali metal and alkaline earth metal hydrides, e.g. sodium hydride; and organolithium and organomagnesium compounds.

(C) For the preparation of the compounds of formula I in which $R^2$ is chlorine or bromine and $R^4$ is 3-pyridyl, 2-pyrazinyl or 5-pyrimidinyl, an alcohol of the formula

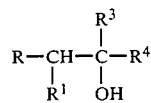
I″ wherein R, $R^1$, $R^3$ and $R^{4'}$ are as previously described is treated with a chlorinating agent or brominating agent.

The chlorination according to this procedure is conveniently carried out as described in European Patent Publication No. 74018, page 9, lines 1–20 for an analogous chlorination. In the case of the bromination phosphorous tribromide is preferably used as the brominating agent. In principle, the bromination is carried out under the same reaction conditions as for the chlorination. The brominating agent is also preferably used in excess.

(D) For the preparation of the compounds of formula I in which $R^3$ is 1-$C_{2-6}$-alkenyl and $R^4$ is 3-pyridyl, 2-pyrazinyl or 5-pyrimidinyl, an alkyne derivative of the formula

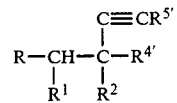
I‴ wherein R, $R^1$, $R^2$ and $R^{4'}$ are as previously defined and $R^{5'}$ is hydrogen or $C_{1-4}$-alkyl, is reduced.

The reduction according to this procedure can be carried out, for example, using elementary hydrogen and a suitable catalyst. This partial alkyne hydrogenation, i.e. the hydrogenation of the alkyne to the alkene by uptake of one molar equivalent of hydrogen, is carried out using conventional methods well known in the art by the appropriate choice of the hydrogenation conditions. An especially suitable catalyst in this connection is palladium, preferably poisoned with lead, silver, magnesium, rhodium or mercury etc. In this manner other reducible groups which may be present in the molecule, e.g. $C_{3-6}$-alkenyl or $C_{3-6}$-alkenylthio ($R^1$), are virtually not hydrogenated, thus concurrent reductions are avoided. Of the poisoned palladium catalysts the Lindlar catalyst [palladium catalyst deactivated with lead; see H. Lindlar, Helv. 35, 446 (b 1952)] is especially preferred.

The catalyst is conveniently present on a carrier such as calcium, strontium or barium carbonate, barium sulfate, carbon, silica gel or aluminium oxide. Moreover, the hydrogenation is conveniently carried out in the presence of a diluent. Examples of diluents include, for example, lower alcohols such as methanol and ethanol, aliphatic and cyclic ethers such as diethyl ether and tetrahydrofuran, acetic acid and its lower alkyl esters, e.g. ethyl acetate, dimethylformamide and pyridine. The hydrogenation is carried out, preferably, at normal pressure in a temperature range of 0°–300° C., and in many cases preferably at room temperature.

In addition to palladium there can, however, be used in the hydrogenation other metal catalysts such as, for example, nickel, especially Raney-nickel which is partially deactivated by storage under ethanol for at least 6 months, Raney-iron and Raney-zinc.

Further, the reduction according to this procedure can be carried out using a complex hydride, preferably diborane (obtainable from sodium borohydride and boron fluoride in situ) or organo-borohydrides. By means of such a hydroboronation the ethyne derivative of formula I''' is converted into the corresponding alken-(1)-yl-borane which is subsequently subjected to a protolysis by the action of a carboxylic acid, preferably acetic acid, to give the corresponding cis-alkene. Examples of organo-borohydrides are bis-[3-methyl-butyl-(2)]borane and 2,3-dimethyl-butyl-(2)-borane [obtainable from diborane and 2-methyl-butene-(2) or 2,3-dimethyl-butene-(2)]. The reaction is conveniently carried out in the presence of a solvent, especially an aliphatic or cyclic ether such as diethyl ether or bis-(2-methoxyethyl)ether (diglyme) in a temperature range between $-80°$ C. and the reflux temperature of the reaction mixture, preferably between 0° C. and room temperature. By means of these methods, which are well known, stereochemically uniform alkenes (cis-alkenes) of high purity can be prepared.

Finally, the reduction according to this procedure can also be carried out by partial electrolysis. This involves a partial electrolytic reduction, which is well known, on cathode materials with a slight over-voltage for hydrogen, such as platinum, nickel, cobalt, silver etc. This reduction is carried out in an aqueous-alcoholic medium in acidic or alkaline solution, in a temperature range of 0°–80° C. and with current densities of about 1–2 amp/dm$^2$, whereby a potential control is recommended.

(E) For the preparation of the compounds of formula I in which R$^4$ is 3-pyridyl 1-oxide, 2-pyrazinyl-1 oxide, 2-pyrazinyl 4-oxide, 2-pyrazinyl, 1,4-dioxide, 5-pyrimidinyl 1-oxide or 5-pyrimidinyl 1,3-dioxide, a pyridine, pyrazine or pyrimidine derivative of the formula

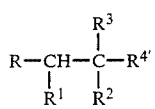  I'''' wherein R, R$^1$, R$^2$, R$^3$ and R$^{4'}$ are as previously defined, is N-oxidized.

The N-oxidation according to this procedure is conveniently carried out under those reaction conditions which are described in European Patent Publication No. 74018, page 10, lines 10–36, for an analogous N-oxidation.

After each of the procedures (A)–(E) a compound of formula I can if desired be converted into the corresponding acid addition salt by reaction with the desired acid in the usual manner.

The isolation and purification of the thus-manufactured compounds of formula I or of the acid addition salts can be carried out according to methods known per se.

The starting materials of general formula II are for the most part novel.

Those ketones of formula II in which R$^1$ is optionally substituted C$_{1-6}$-alkyl, C$_{3-6}$-alkenyl or C$_{3-6}$-alkynyl, as more precisely defined above, can be prepared by treating a ketone of the formula

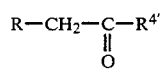  IV wherein R and R$^{4'}$ are as previously defined with a compound of the formula

  V wherein R$^{1'}$ is C$_{1-6}$-alkyl, C$_{3-6}$-alkenyl or C$_{3-6}$-alkynyl optionally substituted with a C$_{1-4}$-alkoxy group and Y is a leaving group, especially chlorine, bromine or iodine.

In the reaction, the ketone of formula IV is advantageously converted with a base such as sodium hydride or lithium diisopropylamide in a diluent, preferably an aprotic organic solvent such as tetrahydrofuran, dimethoxyethane or dimethylformamide, at reaction temperatures between $-70°$ C. and 50° C. into an anion which is then treated with the compound of formula V. The treatment of the ketone of formula IV with the compound of formula V can also be carried out in an aqueous-organic two-phase system in the presence of a phase transfer catalyst, i.e. under the conditions of phase transfer catalysis (see e.g. J. Dockx, Synthesis (1973), 441).

Those ketones of formula II in which R$^1$ is optionally substituted C$_{1-6}$-alkylthio, C$_{3-6}$-alkenylthio, C$_{3-6}$-alkynylthio or arylthio, as more precisely defined above, can be produced by reacting a thioether of the formula

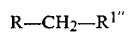  VI wherein R is as previously defined and R$^{1''}$ is C$_{1-6}$-alkylthio, C$_{3-6}$-alkenylthio or C$_{3-6}$-alkynylthio optionally substituted with a C$_{1-4}$-alkoxy group; or arylthio optionally mono, di- or trisubstituted with 1–3 halogen atoms and/or 1 or 2 C$_{1-3}$-alkyl groups and/or 1 or 2 C$_{1-3}$-alkoxy groups and/or a nitro group, with an ester of the formula

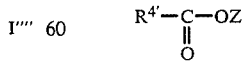  VII wherein R$^{4'}$ is as previously defined and Z is C$_{1-4}$-alkyl or phenyl.

The thioether of formula VI is conveniently treated with a strong base such as an alkali metal amide, e.g. lithium diisopropylamide, in an inert diluent such as a hydrocarbon or an aliphatic or cyclic ether, e.g. tetrahydrofuran, and at a temperature of about −20° C. The addition of a complexing agent, e.g. hexamethylphosphoric acid triamide, to the reaction mixture has been found to be advantageous. The ester of formula VII is subsequently added thereto and the reaction mixture is brought to room temperature. In this manner the reaction is normally completed within a short time.

The starting materials of general formula III are either known or can be produced according to methods known per se.

The starting materials of general formulae I', I'', I''' and I'''' are sub-groups of compounds of formula I. The starting materials of formulae I' and I'' as well as those starting materials of formula I'''' in which $R^2$ is hydroxy can be produced in accordance with procedure A from corresponding starting materials of formulae II and III, while the starting materials of formula I''' in which $R^2$ is chlorine or bromine can be produced in accordance with procedure C from corresponding alcohols of formula I'' and a chlorinating agent or brominating agent. The starting materials of formula I'''' are the end products of procedures A, B, C and D.

The starting materials of general formulae IV, V, VI and VII are either known or can be produced according to methods well known in the art.

The compounds of formula I and their acid addition salts possess fungicidal activity and can accordingly be used for combatting fungi in agriculture and in horticulture. They are especially suitable for eliminating or combatting phytopathogenic fungi on parts of plants, for example, leaves, stems, roots, tubers, fruits or flowers, and on seeds as well as in the soil.

The compounds of formula I are especially effective against *Botrytis cinerea* (grey mold), powdery mildew fungi, such as, for example, *Uncinula necator* (powdery mildew of vines), *Erysiphe cichoracearum* (powdery mildew of cucumbers), *Podosphaera leucotricha* (powdery mildew of apples) and *Erysiphe graminis* (powdery mildew of cereals); *Venturia inaequalis* (apple scab); and harmful fungi of the general Puccinia, Uromyces, Hemileia, Rhizoctonia, Penicillium, Septoria, Corticium, Cercospora, Helminthosporium and Alternaria.

Furthermore, certain compounds of formula I possess a pronounced activity against wood-destroying fungi, such as, for example, *Coniophora puteana* and *Gloeophyllum trabeum*.

The compounds of formula I of the present invention possess local and/or systemic activity.

The compounds of formula I are active under greenhouse conditions even at a concentration of 1 mg to 500 mg of active ingredient per liter of spray liquor. In the open air, they are advantageously applied in concentrations of 25 g to 1000 g of active ingredient of formula 1 per hectare and treatment. For the control of seed-borne fungi in a disinfecting process, 0.025 to 1.5 grams of a compound of formula I per kg of seeds are used.

The invention is also directed to fungicidal compositions which comprise inert carrier material and, as the active ingredient, an effective amount of a compound of formula I or an acid addition salt thereof. These fungicidal compositions contain, as the inert carrier material, at least one of the following ingredients: solid carrier materials; solvents or dispersion media, surface active agents, for example, wetting and emusifying agents; dispersing agents; and stabilizers.

Examples of solid carrier materials include natural mineral substances, such as kaolin, aluminas, siliceous earth, talc, bentonite, chalk, magnesium carbonate, limestone, quartz, dolomite, attapulgite, montmorillonite and diatomaceous earth; synthetic mineral substances, such as highly dispersible silicic acid, aluminium oxide and silicates; organic substances, such as cellulose, starch, urea and synthetic resins; and fertilizers, such as phosphates and nitrates, whereby such carrier substances can be present, for example, as dusts, powders or granulates.

Examples of solvents or dispersion media include: aromatics, such as benzene, toluene, xylenes and alkylnaphthalenes; chlorinated aromatics and chlorinated aliphatic hydrocarbons, such as chlorobenzenes, chloroethylenes and methylene chloride; aliphatic hydrocarbons, such as cyclohexane and paraffins (e.g., petroleum fractions); alcohols, such as butanol and glycol, as well as their ethers and esters; ketones, such as acetone, methyl ethyl ketone, methyl isobutyl ketone and cyclohexanone; strongly polar solvents or dispersion media, such as dimethylformamide, N-methylpyrrolidone and dimethylsulfoxide, whereby such solvents or dispersion media preferably have flash points of at least 30° C. and boiling points of at least 50° C., and water. When water is used as the solvent, organic solvents can also be used as auxiliary solvents.

Included among the solvents or dispersion media are the so-called liquified gaseous extenders or carrier substances. By liquified gaseous extenders or carrier substances are meant liquids which are gaseous at normal temperature and under normal pressure, such as aerosol propellants, e.g., halogenated hydrocarbons (e.g., dichlorodifluoromethane).

Surface active agents, especially emulsifying agents and wetting agents, suitable for use in the fungicidal compositions of this invention can be non-ionic, anionic or cationic compounds.

Examples of non-ionic compounds which can be used include condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

Examples of anionic compounds include soaps: fatty sulfate esters, such as dodecyl sodium sulfate, octadecyl sodium sulfate and cetyl sodium sulfate; alkyl sulfonates, aryl sulfonates and fatty-aromatic sulfonates, such as alkylbenzene sulfonates, for example, calcium dodecylbenzene sulfonate, and butylnaphthalene sulfonates; and more complex fatty sulfonates, for example, the amide condensation products of oleic acid and N-methyltaurine and the sodium sulfonate of dioctyl succinate.

Examples of cationic compounds include alkyldimethylbenzylammonium chlorides, dialkyldimethylammonium chlorides, alkyltrimethylammonium chlorides and ethoxylated quaternary ammonium chlorides.

Dispersing agents suitable for use in the fungicidal compositions of this invention are lignin, sodium and ammonium salts of lignin sulfonic acid, sodium salts of maleic anhydride-diisobutylene copolymers, sodium and ammonium salts of sulfonated polycondensation products of naphthalene and formaldehyde, and sulfite lyes. Dispersing agents, which are especially suitable as thickening or anti-settling agents, include methylcellulose, carboxymethylcellulose, hydroxyethylcellulose, polyvinyl alcohol, alginates, caseinates and blood albumin.

Stabilizers suitable for use in the fungicidal compositions of the present invention include acid-binding agents, such as epichlorohydrin, phenyl glycidyl ether and soya epoxides; antioxidants, such as gallic acid esters and butylhydroxytoluene; UV-absorbers, such as substituted benzophenones, diphenylacrylonitrile acid esters and cinnamic acid esters; and deactivators, such as salts of ethylenediaminotetraacetic acid and polyglycols.

The fungicidal compositions of this invention can contain, in addition to the active substances of formula I, other active substances, such as other fungicidal agents, insecticidal and acaricidal agents, bactericides, plant growth regulators and fertilizers. Such combination compositions are suitable for broadening the spectrum of activity or for specifically influencing plant growth.

The fungicidal compositions of the present invention can be prepared by known methods, for example, by mixing the active ingredient with solid carrier materials, by dissolution or suspension in suitable solvents or dispersion media, and, if necessary, using surface active agents, as wetting or emulsifying agents, or dispersing agents, or by diluting pre-prepared emulsifiable concentrates with solvents or dispersion media.

In preparing the fungicidal compositions of the present invention, the active ingredient of formula I is mixed with inert carrier material. In the case case of pulverous composition, the active ingredient can be mixed with the solid carrier material, for example, by milling together, or the solid carrier material can be impregnated with a solution or suspension of the active ingredient and then the solvent or suspension medium can be removed by evaporation, heating or removing under reduced pressure. By the addition of surface active or dispersing agent, such pulverous compositions can be made readily wettable with water so that they can be converted into aqueous suspensions which are suitable, for example, as spray compositions.

The compounds of formula I can be mixed with a surface active agent and a solid carrier material to form a wettable powder which is dispersible in water, or they can be mixed with a solid pre-granulated carrier material to form a granulate.

For preparation of emulsifiable concentrates which are especially suitable for storage and shipment, the active ingredient can be dissolved in a water-immiscible solvent, such as, for example, an alicyclic ketone, which conveniently contains a dissolved emulsifying agent, so that the solution becomes self-emulsifying upon addition to water. Alternatively, the active ingredient can be mixed with an emulsifying agent, and the mixture can then be diluted with water to the desired concentration. Moreover, the active substance can be dissolved in a solvent, and thereafter the solution can be mixed with an emulsifying agent. Such a mixture can likewise be diluted with water to the desired concentration. In this manner there are obtained emulsifiable concentrates or ready-for-use emulsions.

The fungicidal compositions of this invention generally contain between 0.0001 percent by weight and 95 percent by weight of a compound or compounds of formula I as the active ingredient(s).

The fungicidal compositions of the present invention can be in forms suitable for storage or shipment. In such forms (e.g., emulsifiable concentrates), the concentration of active ingredients is normally at the higher end of the above concentration range. These forms can then be diluted with the same or different carrier materials to afford active ingredient concentrations suitable for practice use, and such concentrations normally lie at the lower end of the above-noted concentration range. Emulsifiable concentrates generally contain from about 5 percent by weight to about 95 percent by weight, preferably from 25 percent by weight to 75 percent by weight, of the compound or compounds of formula I.

The application forms prepared from the above-indicated compositions include ready-for-use solutions, emulsions, foams, suspensions, powders, pastes, soluble powders, dusting agents and granulates.

The concentrations of active ingredient in the ready-for-use preparations can vary over wide limits. In spray liquors, the concentration can be, for example, between 0.0001 percent by weight and 20 percent by weight.

The active ingredients can also be used with good effect in the ultra-low-volume process (ULV) where it is possible to formulate spray liquors having preferably from about 0.5 to about 20 percent by weight of active ingredient.

The active ingredients can also be used with good effect in the Low-Volume process and in the High-Volume process where it is possible to formulate spray liquors having from 0.02 to 1.0 and 0.002 to 0.1 percent by weight of active ingredient, respectively.

The present invention is also concerned with a method for combatting fungi by employing conventional application methods used in plant protection or in agriculture. This method comprises treating the locus to be protected, for example, plants, parts of plants or seeds, with an effective amount of a compound of formula I, an acid addition salt thereof, or a composition containing such compounds.

The following Examples illustrate the invention.

I. MANUFACTURE OF THE ACTIVE SUBSTANCES OF FORMULA I

Example 1

48 ml of n-butyl lithium (1.6 molar in n-hexane) are added dropwise at $-75°$ C. to $-70°$ C. to a solution of 2 g of acetylene in 140 ml of tetrahydrofuran. After 10 minutes reaction at $-75°$ C. a solution of 10.7 g of 2-(2,4-dichlorophenyl)-1-(3-pyridyl)-1-propanone in 20 ml of tetrahydrofuran is added dropwise at $-75°$ C. to $-70°$ C. After a further 100 minutes at $-75°$ C. the cooling is removed and the reaction mixture thereby warms slowly to room temperature. The reaction is stopped by the addition of 30 ml of water, and the aqueous phase which thereby results is thickened to a paste by the introduction of powdered potassium carbonate. The organic phase is decanted off and the inorganic paste is washed three times with 25 ml of diethyl ether each time. After removing the solvent under reduced pressure from the organic phase a brown, highly viscous oil is present. By adding ethyl acetate and n-hexane there is obtained therefrom crystalline α-ethynyl-α-(2,4-dichloro-α-methylbenzyl)-3-pyridylmethanol, m.p. 143° C. (decomposition).

In an analogous manner, from 2-(2,4-dichlorophenyl)-1-(3-pyridyl)-4-penten-1-one and acetylene there is obtained α-ethynyl-α-(α-allyl-2,4-dichlorobenzyl)-3-pyridylmethanol, m.p. 122°-123° C.;

from 2-(2,4-dichlorophenyl)-1-(3-pyridyl)-1-butanone and acetylene there is obtained α-ethynyl-α-(α-ethyl- 2,4-dichlorobenzyl)-3-pyridylmethanol, m.p. 124°–124.5° C.;

from 2-(2,4-dichlorophenyl)-1-(3-pyridyl)-4-pentyn-1-one and acetylene there is obtained α-ethynyl-α-[2,4-dichloro-α-(2-propynyl)-benzyl]-3-pyridylmethanol, m.p. 137°–137.5° C.;

from 2-(2,4-dichlorophenyl)-2-(methylthio)-1-(3-pyridyl)-1-ethanone and acetylene there is obtained α-ethynyl-α-(2,4-dichloro-α-methylthio-benzyl)-3-pyridylmethanol, m.p. 136°–137° C.;

from 2-(2,4-dichlorophenyl)-1-(3-pyridyl)-1-propanone and 1-pentyne there is obtained α-(2,4-dichloro-α-methylbenzyl)-α-(1-pentynyl)-3-pyridylmethanol, m.p. 117°–117.5° C.;

from 2-(2,4-dichlorophenyl)-1-(3-pyridyl)-1-propanol and 1-decyne there is obtained α-(1-decynyl)-α-(2,4-dichloro-α-methylbenzyl)-3-pyridylmethanol as a yellow oil;

from 2-(2,4-dichlorophenyl)-1-(3-pyridyl)-1-propanone and phenylacetylene there is obtained α-(2,4-dichloro-α-methylbenzyl)-α-phenylethynyl-3-pyridylmethanol, m.p. 160° C.;

from 2-(2,4-dichlorophenyl)-1-(3-pyridyl)-1-propanone and ethoxyacetylene there is obtained α-ethoxyethynyl-α-(2,4-dichloro-α-methylbenzyl)-3-pyridylmethanol, m.p. 125° C.;

from 2-(2,4-dichlorophenyl)-1-(3-pyridyl)-1-propanone and 1,1-diethoxypropyne-2 there is obtained α-(3,3-diethoxy-1-propynyl)-α-(2,4-dichloro-α-methylbenzyl)-3-pyridylmethanol, m.p. 117° C.;

from 2-(2,4-dichlorophenyl)-1-(3-pyridyl)-1-propanone and propargyl chloride there is obtained α-(3-chloro-1-propynyl)-α-(2,4-dichloro-α-methylbenzyl)-3-pyridylmethanol, m.p. 127° C.;

from 2-(4-chlorophenyl)-1-(3-pyridyl)-1-propanone and acetylene there is obtained α-ethynyl-α-(4-chloro-α-methylbenzyl)-3-pyridylmethanol, m.p. 113°–119° C.;

from 2-(4-chlorophenyl)-1-(3-pyridyl)-1-propanone and 1,1-diethoxypropyne-2 there is obtained α-(4-chloro-α-methylbenzyl)-α-(3,3-diethoxy-1-propynyl)-3-pyridylmethanol as a yellow oil;

from 2-(2,4-dichlorophenyl)-1-(3-pyridyl)-1-pentanone and acetylene there is obtained α-ethynyl-α-[2,4-dichloro-α-(n-propyl)-benzyl]-3-pyridylmethanol, m.p. 141°–143° C.;

from 2-(2,4-dichlorophenyl)-1-(3-pyridyl)-1-pentanone and 1,1-diethoxypropyne-2 there is obtained α-(3,3-diethoxy-1-propynyl)-α-[2,4-dichloro-α-(n-propyl)-benzyl]-3-pyridylmethanol, m.p. 124°–125° C.;

from 2-(2,4-dichlorophenyl)-1-(2-pyrazinyl)-4-penten-1-one and acetylene there is obtained α-ethynyl-α-(α-allyl-2,4-dichlorobenzyl)-2-pyrazinylmethanol, m.p. 108°–109° C.

Example 2

A solution of 28 g of 2-(2,4-dichlorophenyl)-1-(3-pyridyl)-1-propanone in 50 ml of absolute tetrahydrofuran is added dropwise while cooling with ice so that the reaction temperature does not exceed 30° C. to a Grignard solution prepared from 2.9 g of magnesium shavings and 21 g of 4-bromo-fluorobenzene in 100 ml of absolute tetrahydrofuran. The reaction mixture is stirred at room temperature for 1 hour. 100 ml of 20% aqueous ammonium chloride solution are subsequently added dropwise, and the organic phase is separated, washed with water, dried over anhydrous sodium sulfate and evaporated. In order to remove organic impurities the crystalline residue is treated with warm diethyl ether, filtered and dried. There are obtained 32.2 g (85% of the theoretical yield) of α-(2,4-dichloro-α-methylbenzyl)-α-(p-fluorophenyl)-3-pyridylmethanol, m.p. 187°–188° C.

In an analogous manner, starting from 2-(2,4-dichlorophenyl)-1-(3-pyridyl)-1-propanone and 4-chlorophenylmagnesium chloride there is obtained α-(2,4-dichloro-α-methylbenzyl)-α-(p-chlorophenyl)-3-pyridylmethanol, m.p. 175°–176° C.;

starting from 2-(2,4-dichlorophenyl)-1-(3-pyridyl)-4-penten-1-one and 4-chlorophenylmagnesium chloride there is obtained α-(α-allyl-2,4-dichlorobenzyl)-α-(p-chlorophenyl)-3-pyridylmethanol, m.p. 93°–95° C.;

starting from 2-(2,4-dichlorophenyl)-1-(3-pyridyl)-1-propanone and allylmagnesium bromide there is obtained α-allyl-α-(2,4-dichloro-α-methylbenzyl)-3-pyridylmethanol, $n_D^{25}$: 1.5756;

starting from 2-(2,4-dichlorophenyl)-1-(3-pyridyl)-1-propanone and vinylmagnesium bromide there is obtained α-(2,4-dichloro-α-methylbenzyl)-α-vinyl-3-pyridylmethanol, m.p. 154°–156° C.;

starting from 2-(2,4-dichlorophenyl)-1-(3-pyridyl)-4-penten-1-one and vinylmagnesium bromide there is obtained α-(α-allyl-2,4-dichlorobenzyl)-α-vinyl-3-pyridylmethanol, m.p. 154°–156° C.;

starting from 2-(2,4-dichlorophenyl)-2-methylthio-1-(3-pyridyl)-1-ethanone and vinylmagnesium bromide there is obtained α-(2,4-dichloro-α-methylthio-benzyl)-α-vinyl-3-pyridylmethanol, m.p. 132°–133.5° C.;

starting from 2-(2,4-dichlorophenyl)-1-(3-pyridyl)-1-propanone and 1-propenylmagnesium bromide there is obtained α-(2,4-dichloro-α-methylbenzyl)-α-(1-propen-1-yl)-3-pyridylmethanol, m.p. 115°–119°;

starting from 2-(2,4-dichlorophenyl)-1-(3-pyridyl)-1-propanone and 2-propenylmagnesium bromide there is obtained α-(2,4-dichloro-α-methylbenzyl)-α-isopropenyl-3-pyridylmethanol, m.p. 169°–171° C.

Example 3

150 mg of α-ethynyl-α-(2,4-dichloro-α-methylbenzyl)-3-pyridylmethanol are dissolved in 1.5 ml of thionyl chloride and stirred at room temperature for 30 minutes. The reaction mixture is thereafter concentrated, added to ice-water and neutralized with saturated sodium bicarbonate solution. Extraction with ethyl acetate yields, after drying over anhydrous sodium sulfate and complete evaporation of the organic phase, 3-[1-chloro-1-(2,4-dichloro-α-methylbenzyl)-2-propynyl]-pyridine as a yellow oil.

In an analogous manner, from α-(2,4-dichloro-α-methylbenzyl-α-(1-pentynyl)-3-pyridylmethanol and thionyl chloride there is obtained 3-[1-chloro-1-(2,4-dichloro-α-methylbenzyl)-2-hexynyl]-pyridine as a yellow oil;

from α-(1-decynyl)-α-(2,4-dichloro-α-methylbenzyl)-3-pyridylmethanol and thionyl chloride there is obtained 3-[1-chloro-1-(2,4-dichloro-α-methylbenzyl)-2-undecynyl]-pyridine as a yellow oil.

Example 4

A solution of 1 g of α-ethynyl-α-(2,4-dichloro-α-methylbenzyl)-3-pyridylmethanol in 10 ml of methanol is treated at 10° C. with 1.4 ml of 28% aqueous sodium hydroxide solution and 0.83 g of iodine. The reaction solution is stirred at 15°–20° C. for 4 hours and freed from solvent under reduced pressure. The residue is taken up in ethyl acetate and washed with saturated sodium chloride solution. After drying the organic phase over anhydrous sodium sulfate the solvent is removed therefrom in a water-jet vacuum and α-(2,4-dichloro-α-methylbenzyl)-α-iodoethynyl-3-pyridylmethanol, m.p. 160° C., is crystallized from the residue by the addition of ethyl acetate and n-hexane.

In an analogous manner, from α-ethynyl-α-(α-ethyl-2,4-dichlorobenzyl)-3-pyridylmethanol and iodine there is obtained α-(α-ethyl-2,4-dichlorobenzyl)-α-iodoethynyl-3-pyridylmethanol, m.p. 173° C.;

from α-ethynyl-α-(2,4-dichloro-α-methylbenzyl)-3-pyridylmethanol and bromine there is obtained α-bromoethynyl-α-(2,4-dichloro-α-methylbenzyl)-3-pyridylmethanol, m.p. 131°–132° C. (decomposition);

from α-ethynyl-α-(α-allyl-2,4-dichlorobenzyl)-2-pyrazinylmethanol and iodine there is obtained α-(α-allyl-2,4-dichlorobenzyl)-α-iodoethynyl-2-pyrazinylmethanol, m.p. 123°–125° C.

Example 5

A solution of 2.45 g of α-(2,4-dichloro-α-methylbenzyl)-α-(1-pentynyl)-3-pyridylmethanol in 100 ml of methanol is stirred with 60 mg of Lindlar catalyst (4.6% palladium and 4.6% lead(II) hydroxide on calcium carbonate) in a hydrogen atmosphere at normal pressure for 7 hours. After each hour has passed there are added a further 60 mg of Lindlar catalyst, i.e. a total of a further 300 mg. The catalyst is thereafter filtered off, the solvent is distilled off under reduced pressure and the residual, colourless oil is crystallized by the addition of n-hexane. There is obtained α-(2,4-dichloro-α-methylbenzyl)-α-[(Z)-1-pentenyl]-3-pyridylmethanol as colourless crystals, m.p. 115°–116° C.

II. FORMULATION EXAMPLES

Example 6

1. Spray powder (for active substances which are liquid or which melt below 75° C.)

|  | Parts by weight |
| --- | --- |
| Active substance of formula I | 50 |
| Hydrated silicic acid | 37 |
| Kaolin | 5 |
| Alkylphenol ethoxylate | 4 |
| Sodium polynaphthalenesulfonate | 4 |
|  | 100 |

The liquid or molten active substance is taken up on the silicic acid, the remaining components are admixed and the mixture is finely ground in a suitable mill.

2. Spray powder (for solid active substances which melt above 75° C.)

|  | Parts by weight |
| --- | --- |
| Active substance of formula I | 50 |
| Hydrated silicic acid | 5 |
| Kaolin | 42 |
| Sodium lauryl sulfate | 1 |
| Sodium lignosulfonate | 2 |
|  | 100 |

The components are mixed with one another and the mixture is then finely ground in a suitable mill.

Example 7

Emulsifiable concentrate (for active substances which are liquid at 20°–25° C.)

|  | Parts by weight |
| --- | --- |
| Active substance of formula I | 500 |
| Castor oil ethoxylate | 100 |
| Calcium dodecylbenzenesulfonate | 25 |
| Mixture of $C_{10}$—alkylbenzenes ad | 1000 parts by vol. |

The components are mixed with one another until a clear solution is obtained.

What is claimed is:

1. A compound of the formula

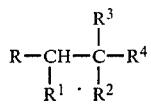

wherein

R is mono-, di- or trisubstituted phenyl, the substituents being selected from the group consisting of halogen, $C_{1-3}$-alkyl, $C_{1-3}$-alkoxy and combinations thereof with the proviso that there are no more than two of the alkyl or alkoxy substituents on the trisubstituted phenyl;

$R^1$ is $C_{1-6}$-alkyl, $C_{3-6}$-alkenyl, $C_{3-6}$-alkynyl, phenylthio, $C_{1-6}$-alkylthio, $C_{3-6}$-alkenylthio, $C_{3-6}$-alkynylthio, $C_{3-6}$-alkynylthio monosubstituted with $C_{1-4}$-alkoxy, or a mono-, di- or trisubstituted phenylthio, the substituents being selected from the group consisting of halogen, $C_{1-3}$-alkyl, $C_{1-3}$-alkoxy, nitro and combinations thereof with the proviso that there is no more than one nitro substituent on the di- or trisubstituted phenylthio and that there are no more than two $C_{1-3}$-alkyl or $C_{1-3}$-alkoxy substituents on the trisubstituted phenylthio;

$R_2$ is hydroxy; $R^3$ is $C_{2-6}$-alkenyl, —C≡$CR^5$, phenyl-$C_{1-3}$-alkyl or mono-, di- or trisubstituted phenyl-$C_{1-3}$-alkyl, the substituents being selected from the group consisting of halogen, $C_{1-3}$-alkyl, $C_{1-3}$-alkoxy, nitro and combinations thereof with the proviso that there is no more than one nitro substituent on the di- or trisubstituted phenyl-$C_{1-3}$-alkyl and that there are no more than two $C_{1-3}$-alkyl or $C_{1-3}$-alkoxy substituents on the trisubstituted phenyl-$C_{1-3}$-alkyl;

$R^4$ is 3-pyridyl or 3-pyridyl 1-oxide; and $R^5$ is hydrogen, phenyl, vinyl, bromine, iodine, $C_{1-6}$-alkoxy, $C_{1-10}$-alkyl, $C_{1-10}$-alkyl disubstituted with $C_{1-3}$-alkoxy, $C_{1-10}$-alkyl monosubstituted with $C_{1-3}$-alkoxy, chlorine or bromine, or mono-, di- or trisubstituted phenyl, the substituents being selected from the group consisting of halogen, $C_{1-3}$-alkyl, $C_{1-3}$-alkoxy and combinations thereof with the proviso that there are no more than two of the alkyl or alkoxy substituents on the trisubstituted phenyl; or an acid addition salt thereof.

2. The compound according to claim 1, wherein R is 2,4-dichlorophenyl.

3. The compound according to claim 2, wherein $R^4$ is 3-pyridyl.

4. The compound according to claim 1, selected from the group consisting of
α-ethynyl-α-(2,4-dichloro-α-methylbenzyl)-3-pyridylmethanol,
α-(2,4-dichloro-α-methylbenzyl)-α-(1-pentynyl)-3-pyridylmethanol, α-(2,4-dichloro-α-methylbenzyl)-α-iodoethynyl-3-pyridylmethanol,
α-(2,4-dichloro-α-methylbenzyl)-α-vinyl-3-pyridylmethanol,
α-ethynyl-α-(2,4-dichloro-α-methylthio-benzyl)-3-pyridylmethanol,
α-ethoxyethynyl-α-(2,4-dichloro-α-methylbenzyl)-3-pyridylmethanol,
α-ethynyl-α-[2,4-dichloro-α-(2-propynyl)-benzyl]-3-pyridylmethanol,
α-(2,4-dichloro-α-methylbenzyl)-α-(1-propen-1-yl)-3-pyridylmethanol and
α-(2,4-dichloro-α-methylbenzyl)-α-isopropenyl-3-pyridylmethanol.

5. The compound according to claim 1, selected from the group consisting of
α-ethynyl-α-(α-allyl-2,4-dichlorobenzyl)-3-pyridylmethanol,
α-ethynyl-α-(α-ethyl-2,4-dichlorobenzyl)-3-pyridylmethanol,
α-(1-decynyl)-α-(2,4-dichloro-α-methylbenzyl)-3-pyridylmethanol,
α-(2,4-dichloro-α-methylbenzyl)-α-phenylethynyl-3-pyridylmethanol,
α-(3,3-diethoxy-1-propynyl)-α-(2,4-dichloro-α-methylbenzyl)-3-pyridylmethanol,
α-(3-chloro-1-propynyl)-α-(2,4-dichloro-α-methylbenzyl)-3-pyridylmethanol,
α-allyl-α-(2,4-dichloro-α-methylbenzyl)-3-pyridylmethanol,
α-(α-allyl-2,4-dichlorobenzyl)-α-vinyl-3-pyridylmethanol,
α-(2,4-dichloro-α-methylthio-benzyl)-α-vinyl-3-pyridylmethanol,
α-(α-ethyl-2,4-dichlorobenzyl)-α-iodoethynyl-3-pyridylmethanol and
α-bromoethynyl-α-(2,4-dichloro-α-methylbenzyl)-3-pyridylmethanol.

6. The compound according to claim 1, selected from the group consisting of
α-ethynyl-α-(4-chloro-α-methylbenzyl)-3-pyridylmethanol,
α-(4-chloro-α-methylbenzyl)-α-(3,3-diethoxy-1-propynyl)-3-pyridylmethanol,
α-(3,3-diethoxy-1-propynyl)-α-[2,4-dichloro-α-(n-propyl)benzyl]-3-pyridylmethanol,
α-(2,4-dichloro-α-methylbenzyl)-α-[(Z)-1-pentenyl]-3-pyridylmethanol.

7. A fungicidal composition comprising a compatible carrier material and, as the active ingredient, an amount which is effective as a fungicide of a compound according to claim 1.

8. A fungicidal composition according to claim 1 comprising an effective amount of a compound selected from the group consisting of
α-ethynyl-α-(2,4-dichloro-α-methylbenzyl)-3-pyridylmethanol,
α-(2,4-dichloro-α-methylbenzyl)-α-(1-pentynyl)-3-pyridylmethanol,
α-(2,4-dichloro-α-methylbenzyl)-α-iodoethynyl-3-pyridylmethanol,
α-(2,4-dichloro-α-methylbenzyl)-α-vinyl-3-pyridylmethanol,
α-ethynyl-α-(2,4-dichloro-α-methylthio-benzyl)-3-pyridylmethanol,
α-ethoxyethynyl-α-(2,4-dichloro-α-methylbenzyl)-3-pyridylmethanol,
α-ethynyl-α-[2,4-dichloro-α-(2-propynyl)-benzyl]-3-pyridylmethanol,
α-(2,4-dichloro-α-methylbenzyl)-α-(1-propen-1-yl)-3-pyridylmethanol and
α-(2,4-dichloro-α-methylbenzyl)-α-isopropenyl-3-pyridylmethanol.

9. A fungicidal composition according to claim 1 comprising an effective amount of α-(2,4-dichloro-α-methylbenzyl)-α-[(Z)-1-pentenyl]-3-pyridylmethanol.

10. A method for combatting plant fungi which comprises treating the locus to be protected with an effective amount of a compound in accordance with claim 1.

11. A method for combatting plant fungi which comprises treating the locus to be protected with an effective amount of a compound in accordance with claim 2.

12. A method for combatting plant fungi which comprises treating the locus to be protected with an effective amount of a compound in accordance with claim 3.

13. A method for combatting plant fungi which comprises treating the lens to be protected with an effective amount of a compound in accordance with claim 4.

14. A method for combatting plant fungi which comprises treating the lens to be protected with an effective amount of a compound in accordance with claim 5.

15. A method for combatting plant fungi which comprises treating the locus to be protected with an effective amount of a compound in accordance with claim 6.

16. A method for combatting plant fungi which comprises treating the lens to be protected with an effective amount of a composition in accordance with claim 7.

17. A method for combatting plant fungi which comprises treating the locus to be protected with an effective amount of a composition in accordance with claim 8.

18. A method for combatting plant fungi which comprises treating the locus to be protected with an effective amount of a composition in accordance with claim 9.

19. The compound according to claim 1, selected from the group consisting of
α-ethynyl-α-(4-chloro-α-methylbenzyl)-3-pyridylmethanol,
α-(4-chloro-α-methylbenzyl)-α-(3,3-diethoxy-1-propynyl)-3-pyridylmethanol,
α-ethynyl-α-[2,4-dichloro-α-(n-propyl)-benzyl]-3-pyridylmethanol,
α-(3,3-diethoxy-1-propynyl)-α-[2,4-dichloro-α-(n-propyl)-benzyl]-3-pyridylmethanol, and
α-(2,4-dichloro-α-methylbenzyl)-α-[(Z)-1-pentenyl]-3-pyridylmethanol.

* * * * *